United States Patent [19]

Tone et al.

[11] Patent Number: 5,028,698

[45] Date of Patent: Jul. 2, 1991

[54] CYTORHODIN S DERIVATIVES AND A PROCESS FOR THEIR PREPARATION

[75] Inventors: Yukiko Tone; Toshiro Iwahashi; Etsuko Ohkouchi; Hiroshi Kitagawa; Isamu Sugawara, all of Saitama; Hiroshi Okazaki; Akio Fukuda, both of Tokyo, all of Japan; Hans G. Berscheid, Schwalbach, Fed. Rep. of Germany; Hitoko Numata, Saitama, Japan; Junko Usui, Saitama, Japan; Shunji Senda, Saitama, Japan; Akihiko Matsuo, Saitama, Japan; Hiroshi Watanabe, Saitama, Japan; Itsuo Kurobane, Saitama, Japan

[73] Assignee: Hoechst Japan Limited, Tokyo, Japan

[21] Appl. No.: 464,695

[22] Filed: Jan. 18, 1990

Related U.S. Application Data

[63] Continuation of Ser. No. 65,608, Jun. 23, 1987, abandoned.

[30] Foreign Application Priority Data

Jun. 25, 1986 [JP] Japan .................. 61-147119
Mar. 30, 1987 [JP] Japan .................. 62-74259

[51] Int. Cl.$^5$ .................. C07K 3/00; C07H 15/24
[52] U.S. Cl. .................. 530/391; 530/389; 536/6.4; 536/18.5
[58] Field of Search .......... 536/6.4, 18.5; 530/389, 530/391

[56] References Cited

U.S. PATENT DOCUMENTS 4,737,583 4/1988 Huber et al. .................. 536/6.4

Primary Examiner—Elli Peselev
Attorney, Agent, or Firm—Finnegan, Henderson, Farabow, Garrett and Dunner

[57] ABSTRACT

Cytorhodin S derivatives, especially cytorhodin S-immunoglobulin complexes are disclosed. Cytorhodin S possesses very high anticancer activity, but the complexes act more selectively on cancer cells and are more useful as an anticancer agent. New intermediate derivatives are also useful as an anticancer agent.

15 Claims, 4 Drawing Sheets

CYTORHODIN S DERIVATIVES AND A PROCESS FOR THEIR PREPARATION

This application is a continuation application of Ser. No. 07/065,608 filed June 23, 1987, and now abandoned.

The present invention relates to cytorhodin S derivatives, particularly to cytorhodin S-immunoglobulin complexes.

The cytorhodin S derivatives of the invention selectively act on cancer cells and are useful as an anticancer agent.

It is reported that cytorhodin S is prepared by the acid treatment of a crude cytorhodin mixture produced by cultivating Streptomyces Y-11472 (deposition No. DSM-2658) and is of anticancer activities (Japanese Patent Laid-Open Sho 60-48994). Although cytorhodin S itself possesses very high anticancer activities, it is still desired to develop agents which selectively act on cancer cells and have high bioavailability.

As a result of extensive studies on the development of cytorhodin S derivatives that are superior in selective specificity to cancer cells, we have succeeded to get cytorhodin S-immunoglobulin complexes which maintain the anticancer activities of cytorhodin S itself. The present invention has been completed on the basis of the above finding.

According to the invention, there are provided cytorhodin S derivatives, processes for their preparation and an anticancer agent containing them as follows:

1) A cytorhodin S derivative represented by the general formula (I)

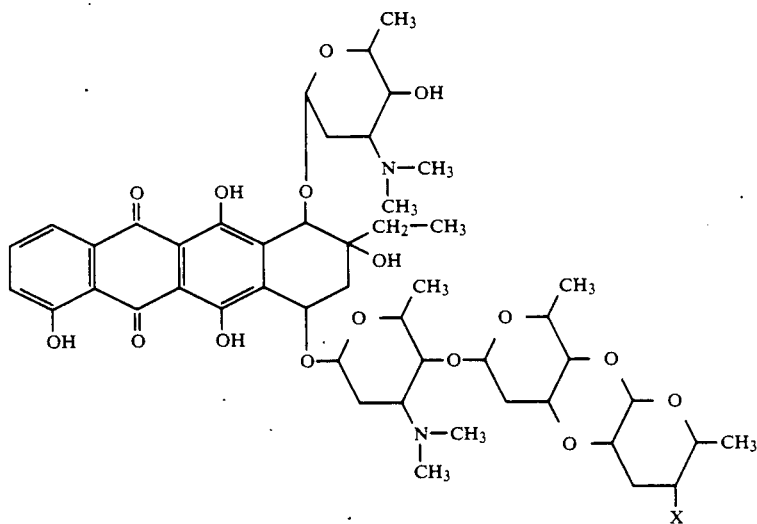

(I)

wherein X represents a group having the formula $-NH_2$, $-NH-R^1-NH_2$, $-NH-R^1-COOH$,

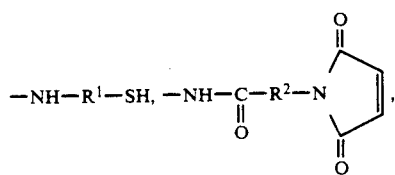

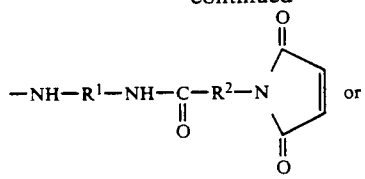

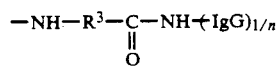

in which $R^1$ represents a divalent hydrocarbon group, which may be substituted with any substituents, $R^2$ is a divalent hydrocarbon group, $R^3$ represents a divalent organic group, IgG represents an immunoglobulin moiety and n represents an integer of 1-15 and salts thereof.

2) A cytorhodin S derivative according to above item 1) wherein $R^3$ represents $R^1$ or a group having the formula

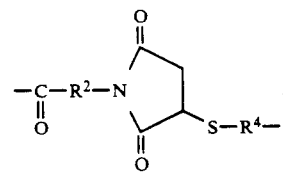

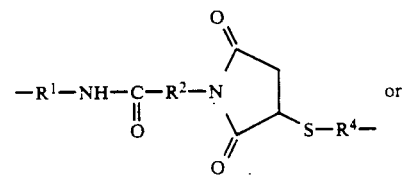

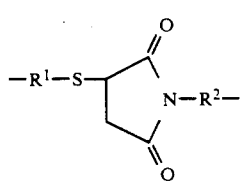

wherein $R^4$ represents a divalent hydrocarbon group.

3) A cytorhodin S derivative according to above item 2) wherein $R^2$ is propylene group and $R^4$ is methylene group.

4) A cytorhodin S derivative according to any of above items 1) to 3) wherein n is 5-12.

5) A cytorhodin S derivative according to any of above items 1) to 4) wherein the IgG is a moiety of the antibody against carcinoembryonic antigen (CEA).

6) A process for preparing a cytorhodin S derivative of the general formula (I) wherein X represents a group having the formula $-NH_2$, $-NH-R^1-NH_2$,

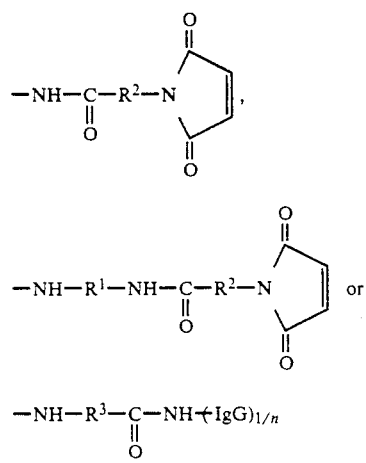

$$-NH-R^3-C(=O)-NH(IgG)_{1/n}$$

wherein $R^1$ represents a divalent hydrocarbon group which may be substituted with any substituents, $R^2$ represents a divalent hydrocarbon group $R^3$ represents a divalent organic radical, IgG represents an immunoglobulin moiety and n represents an integer of 1-15 which comprises reducing a cytorhodin S having the formula (II)

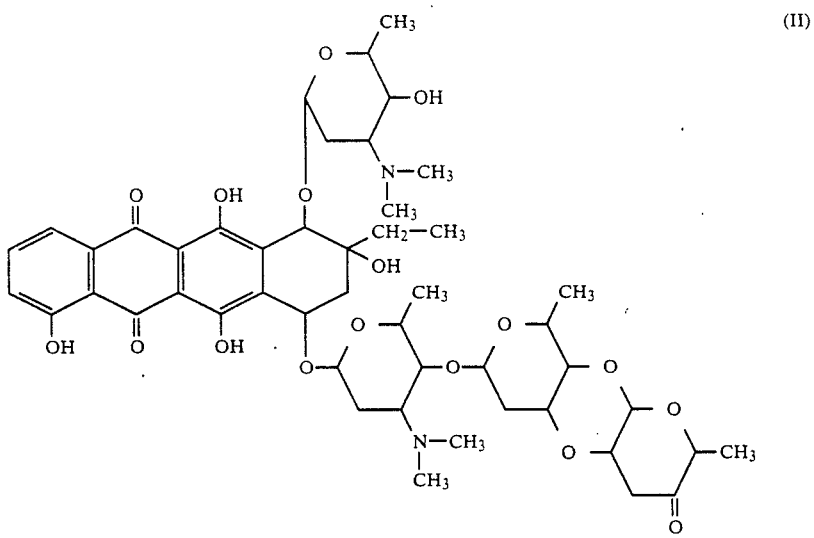

with an alkali metal cyanoborohydride in the presence of an ammonium salt or a compound represented by $NH_2-R^1-NH_2$ wherein $R^1$ has the same meaning as defined above to obtain a cytorhodin S derivative wherein X in the above-mentioned formula (I) is $-NH_2$ or $-NH-R^1-NH_2$m if necessary reacting the product with a maleimide compound having the formula (III)

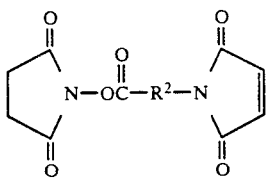 (III)

wherein $R^2$ has the same meaning as defined above to give a cytorhodin S derivative (I) wherein X is

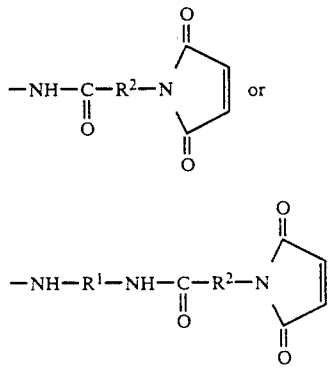

and further, if necessary, reacting the product with a thiolated immunoglobulin having the formula (IV)

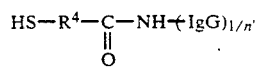 (IV)

wherein $R^4$ represents a divalent hydrocarbon group, IgG has the same meaning as defined above and n' represents an integer of 1-20 to give a cytorhodin S derivative (I) wherein X is

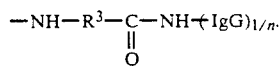

7) A process for preparing a cytorhodin S derivative according to above item 6) wherein $R^3$ is

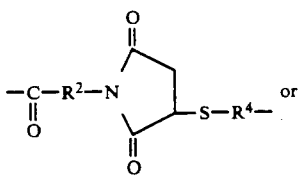

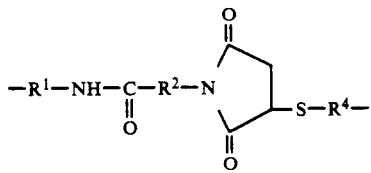

8) A process for preparing cytorhodin S derivative of the general formula (I) wherein X represents a group having —NH—R$^1$—SH or

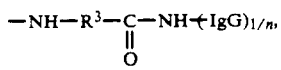

in which R$^1$ represents a divalent hydrocarbon group which may be substituted with any substituents, R$^3$ represents a divalent organic group, IgG represents an immunoglobulin moiety and n represents an integer of 1-15 which comprises reducing a cytorhodin S having the above-mentioned formula (II) with an alkali metal cyanoborohydride in the presence of a compound represented by NH$_2$—R$^1$—SH wherein R$^1$ has the same meaning as defined above to give a cytorhodin S derivative (I) wherein X in the above-mentioned formula (I) is —NH—R$^1$—SH and, if necessary, reacting the product with a maleimidated immunoglobulin having the formula (V)

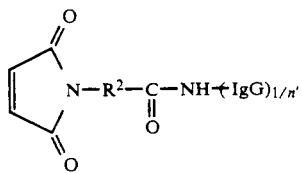

wherein R$^2$ and IgG have the same meanings as defined above and n' represents an integer of 1-20 to give a cytorhodin S derivative (I) wherein X is

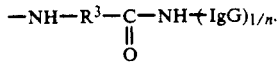

9) A process for preparing a cytorhodin S derivative according to above item 8) wherein R$^3$ is

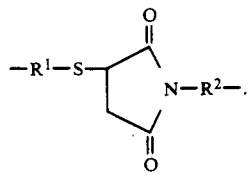

10) A process for preparing a cytorhodin S derivative of the general formula (I) wherein X represents a group having —NH—R$^1$—COOH or

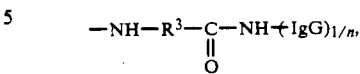

in which R$^1$ represents a divalent hydrocarbon group which may be substituted with any substituents, R$^3$ represents a divalent organic group, IgG represents an immunoglobulin moiety and n represents an integer of 1-15 which comprises reducing cytorhodin S having the above-mentioned formula (II) with an alkali metal cyanoborohydride in the presence of a compound represented by NH$_2$—R$^1$—COOH wherein R$^1$ has the same meaning as defined above and, if necessary, reacting the product with an immunoglobuin having the formula (VI)

    (VI)

wherein IgG has the same meaning as defined above and n represents an integer of 1-15 t- give a cytorhodin S derivative (I) wherein X in the formula (I) is

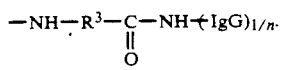

11) A process for preparing a cytorhodin S derivative according to above item 10) wherein R$^3$ is R$^1$.

12) An anticancer agent comprising a cytorhodin S derivative represented by the above-mentioned formula (I).

DETAILED DESCRIPTION OF THE INVENTION

Figure 1:
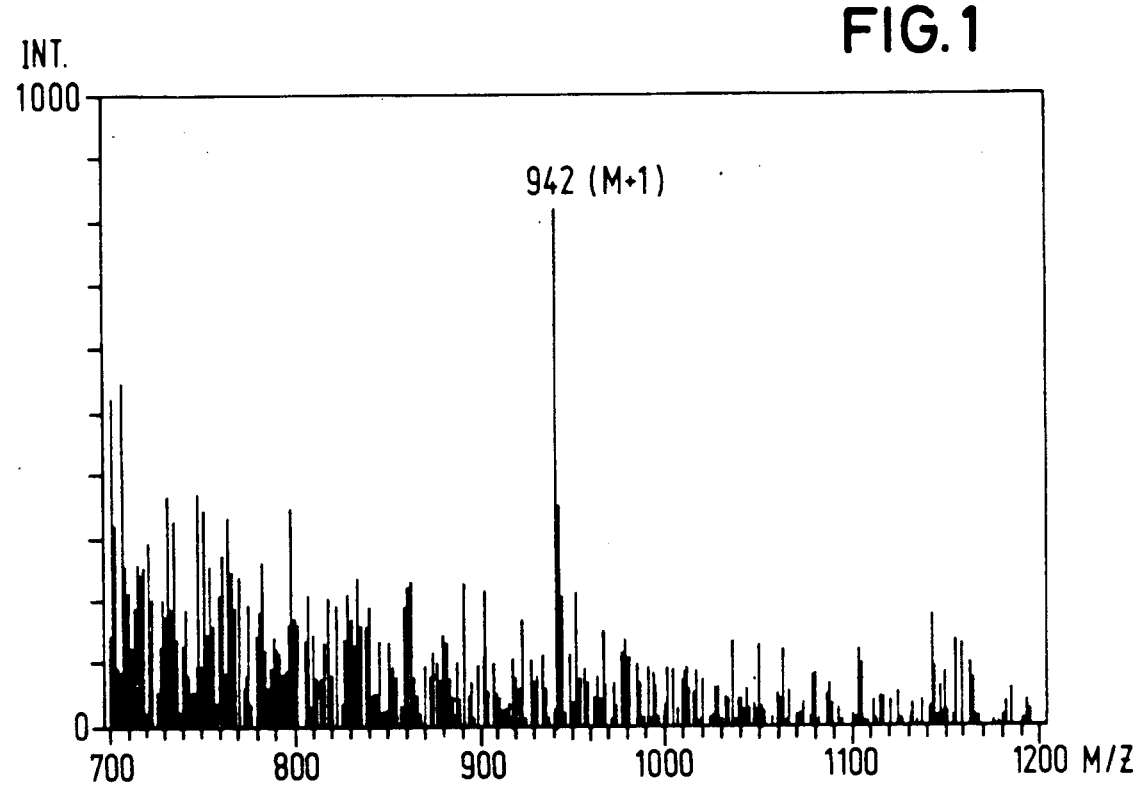
FIG. 1 shows mass spectrum of cytorhodin S amino derivative.
Figure 2:
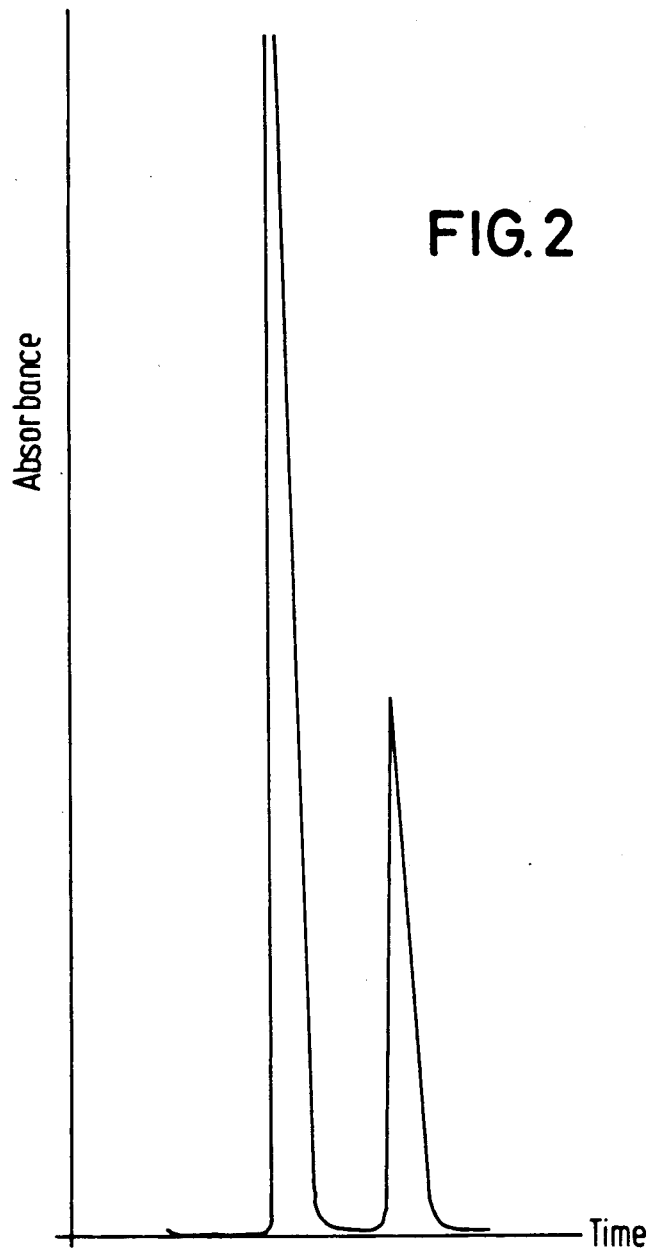
FIG. 2 shows elution patterns of the cytohodin S-immunoglobulin complex and cytorhodin S by column chromatography.

As preferred examples of R$^1$ in the above-mentioned formula (I) are mentioned groups derived from known α-amino acids, β, γ- and ε-amino acids and β, γ- and ε-thiolamines.

As preferred examples of R$^2$ in the above formula (I) are mentioned lower alkylene groups such as methylene, ethylene and propylene, phenylene groups such as p-phenylene and m-phenylene, C$_4$-C$_7$ cycloalkylene groups such as cyclohexylene, phenylenyl lower alkyl groups such as phenylenylmethyl and C$_4$-C$_7$ cycloalkenyl-lower-alkyl groups such as cyclohexylenylmethyl. As preferred examples of $R^3$ are mentioned groups represented by the formulae $$-\overset{O}{\underset{\|}{C}}-R^2-N\underset{\underset{O}{\|}}{\overset{\overset{O}{\|}}{\diagdown}}\hspace{-6pt}\diagup S-R^4-,$$

$$-R^1-NH-\overset{O}{\underset{\|}{C}}-R^2-N\underset{\underset{O}{\|}}{\overset{\overset{O}{\|}}{\diagdown}}\hspace{-6pt}\diagup S-R^4-,$$

$$-R^1-S\diagdown\hspace{-6pt}\diagup\underset{\underset{O}{\|}}{\overset{\overset{O}{\|}}{\diagdown}}N-R^2- \text{ or } -R^1-.$$

As preferred examples of $R^4$ are mentioned lower alkylene groups such as methylene, ethylene and propylenes, phenylene groups such as p-phenylene and m-phenylene groups, $C_4$-$C_7$ cycloalkylene groups such as cyclohexylene, phenylenyl lower alkyl groups such as phenylenylmethyl and $C_4$-$C_7$ cycloalkylennyl lower alkyl groups such as cyclohexylenylmethyl. The immunoglobulin moiety represented by IgG means an immunoglobulin moiety wherein n amino groups are removed from an immunoglobulin. IgG in the formula (I) includes one in which some of the thiol groups $$(-NH-\underset{\underset{O}{\|}}{C}-R^2-SH)$$

introduced to the immunoglobulin remain. This is because not all of the thiol groups in the thiolated immunoglobulin (IV) are reacted with the cytorhodin S derivative and some of the thiol groups remain unreacted.

As the immunoglobulin moiety is preferred antibody that combines specifically with cancer cells.

1/n Indicates the number of the immunoglobulin molecules per molecule of cytorhodin S, which is from 1/1 to 1/15. It means that 1-15 molecules of the cytorhodin S are bound to one molecule of the immunoglobulin.

A compound represented by the formula (I) wherein X is $-NH_2$, $-NH-R^1-NH_2$, $-NHR^1-COOH$, $-NHR^1-SH$, $$-NH-\overset{O}{\underset{\|}{C}}-R^2-N\underset{\underset{O}{\|}}{\overset{\overset{O}{\|}}{\diagdown}}\hspace{-6pt}\diagup \text{ or}$$

$$-NH-R^1-\overset{O}{\underset{\|}{C}}-R^2-N\underset{\underset{O}{\|}}{\overset{\overset{O}{\|}}{\diagdown}}\hspace{-6pt}\diagup$$

is an intermediate compound for preparing the immunoglobulin complexes, which, of course, maintains anticancer activities of cytorhodin S and can also be an anticancer agent as it is.

In producing a complex between an anticancer agent and immunoglobulin, in general, the anticancer agent is bound to the immunoglobulin by means of a bifunctional cross-linking reagent, a condensing agent or a spacer. The above objective is achieved by combining an anticancer agent with a bifunctional cross-linking reagent, a condensing agent or a spacer via a functional group (such as amino carboxyl or thiol group) of the former. Cytorhodin S, however, has none of such functional groups and should necessarily be chemically modified to prepare a derivative containing amino, carboxyl or thiol group. In order to produce such derivatives of cytorhodin S without losing its anticancer activities, the oxo group on the saccharide chain can be converted to amino group. General methods for the reduction of oxo group involve use of lithium aluminum hydride ($LiAlH_4$), sodium borohydride ($NaBH_4$) or the like. The reagent that can be used for selectively reducing the oxo group on the saccharide chain without reducing the oxo group on the anthracyclin ring is sodium cyanoborohydride ($NaBCNH_3$) or lithium cyanoborohydride ($LiBCNH_3$). When such reducing agent is employed in the presence of an ammonium salt or an organic compound containing amino group, the oxo group on the saccharide chain is selectively reduced to amino group thereby producing the derivative of cytorhodin S. In fact, cytorhodin S having the formula (II)

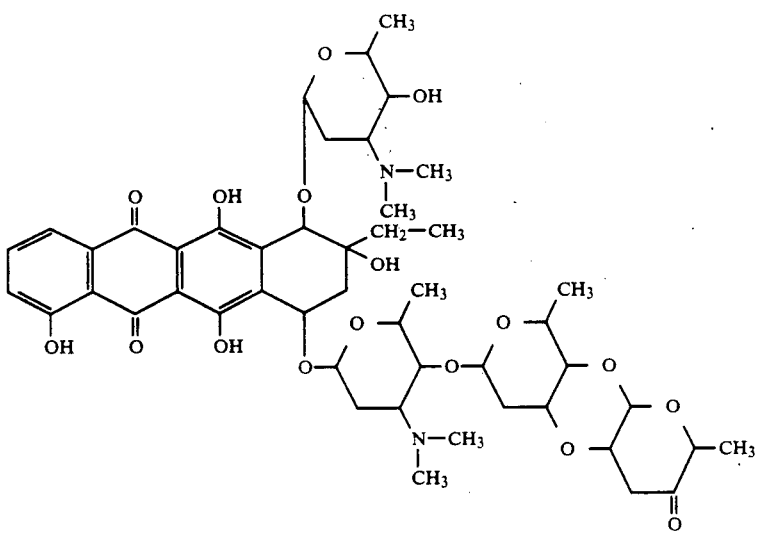

(II)

is converted to a cytorhodin S derivative (I) in which X is —NH₂ or —NH—R¹—NH₂, —NH—R¹—COOH, —NHR¹—SH by the reduction with an alkali metal cyanoborohydride in the presence of an ammonium salt or an organic compound containing an amino group represented by NH₂—R¹—NH₂, NH₂—R¹—COOH, or NH₂—R¹—SH.

Examples of the ammonium salt include ammonium acetate, ammonium propionate and ammonium chloride. As examples of the amino group containing organic compound are mentioned known α-amino acids such as lysine and cysteine, β-, γ- and ε-amino acids such as γ-aminobutyric acid, amino acid esters such as ethyl ester of glycine, and thiolamines such as aminoethanethiol and aminothiophenol. Examples of the alkali metal cyanoborohydride include lithium (or sodium) cyanoborohydride.

The above reaction is easily carried out by dissolving cytorhodin S and an ammonium salt or an amino group-containing organic compound in a water-miscible organic solvent (such as, for example, methanol or ethanol) or in a buffer solution containing none of primary and secondary amines which is adjusted to pH 8 (such as, for example, a phosphate or borate buffer or 2,4,6-trimethylpyridine-hydrochloric acid buffer) and adding to the solution an alkali metal cyanoborohydride at room temperature or under ice-cooling.

The product in the reaction mixture can recovered by conventional means. For example, it is recovered by adjusting the reaction mixture to pH 8, extracting it with a suitable organic solvent such as dichloromethane and distilling off the solvent from the extract or by means of a preparative HPLC.

The amino derivative of cytorhodin S thus produced in which X is —NH₂ or —NH—R¹—NH₂ is then reacted with a maleimide compound having the above formula (III) to give a cytorhodin S derivative having the above formula (I) wherein X is

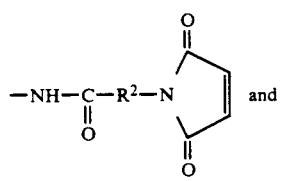 and

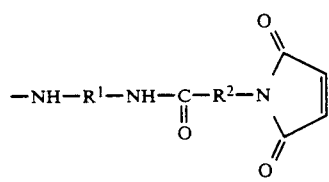

As a by-product is formed N-hydroxysuccinimide.

As examples of the maleimide compound (III) are mentioned N-γ-maleimidobutyryloxy-succinimide [GMBS, R²⁻(CH₂)₃], succinimidyl 4-(N-maleimidomethyl)-cyclohexanecarboxylate

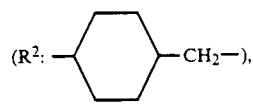

metamaleimidobenzoyl-N-hydroxysuccinimide ester

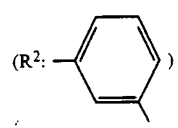

and succinimidyl 4-(p-maleimidophenyl)butyrate

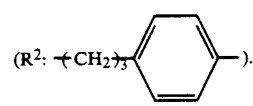

The above reaction may easily be carried out by treating a cytorhodin S amino derivative with a maleimide compound in a suitable solvent (e.g., dichloromethane, dichloroethane, chloroform, pyridine, triethylamine, etc.) at room temperature or under ice-cooling.

The cytorhodin S derivatives thus obtained in which a maleimide group has been introduced are capable of undergoing an addition reaction with any of thiol group-containing proteins or compounds. The double bond of maleimide group participates in the electrophilic addition reaction with thiol group. As described below, therefore, addition reaction between maleimide group and thiol group introduced in immunoglobulin enables formation of a complex.

In general, immunoglobulin used for the preparation of the complex is preferably monoclonal or polyclonal antibody against the membrane protein specifically formed in cancer cells. It is also desirable in clinical application to use the antibody from which the Fc portion has been removed, if a non-human origin antibody is used. However, in consideration of the efficiency in addition of cytorhodin S the entire antibody is preferably employed.

As particularly preferred immunoglobulin is mentioned a monoclonal antibody against cancer-specific protein such as carcinoembryonic antigen (CEA) or α-fetoprotein (AFP). The monoclonal antibody against carcinoembryonic antigen is prepared by a conventional method in which mice are treated with the antigen, the spleen is isolated from the mice, the spleen cells are fused with HAT-sensitive mycloma cells by the polyethylene glycol method, and the hybridoma is selected by using HAT medium as the selective medium and transplanted in mice.

Prior to the reaction of immunogloblin with cytorhodin S having maleimide group for the preparation of a complex, a thiol group is introduced in immunoglobulin. In order to introduce the thiol group, the immunoglobulin is reacted with an N-succinimide compound having the general formula (VII)

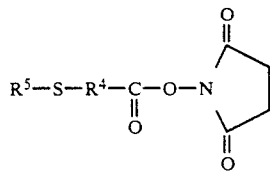

(VII)

wherein $R^4$ is the same meaning as defined above and $R^5$ represents a thiol-protecting group, for example, an acyl group such as acetyl and a 2-pyridylthio group to afford a thiolated immunoglobulin having the above-mentioned formula (IV).

As a preferable example of the N-succinimide compound (VII) is mentioned N-succinimidyl-S-acetyl thioacetate

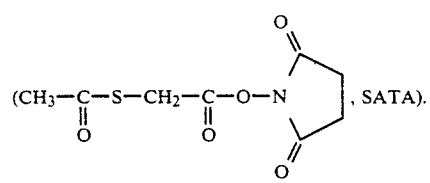, SATA).

SATA is reacted with the amino group in the immunoglobulin to form an amide bond of

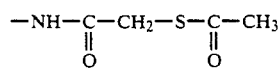

in which the thiol group is protected by an acetyl group, and N-hydroxysuccinimide is formed as a byproduct. Deprotection of the thiol group is effected, for example, with hydroxylamine at pH 7.5 to convert the former to the reactive group

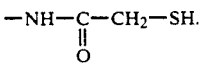

The thio group is apt to be oxidized under certain conditions with a result that immunoglobulin polymers are formed. It is therefore desirable to conduct the deprotection of the acetyl group at 25° C. for about one hour immediately before the reaction with a cytorhodin S derivative having maleimide group.

The thiol group is introduced in a proportion of 1-20, preferably 5-20, per molecule of immunoglobulin depending upon the amount of SATA used. The introduction does not result in loss of antibody activity of the immunoglobulin.

Use of N-succinimidyl 3-(2-pyridyldithio)propionate

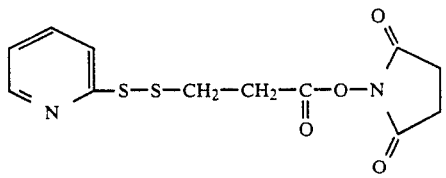

as a thio-introducing reagent in place of the SATA and use of dithiothretol as a deprotecting agent form the group

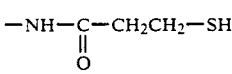

together with the amino group in immunoglobulin.

The immunoglobulin (IV) having thiol group thus produced is reacted with the cytorhodin S having maleimide to prepare the immunoglobulin complex according to the invention.

The above reaction can easily be conducted by admixing a solution of the cytorhodin S derivative having maleimide groups in a water-miscible organic solvent (e.g., methanol, ethanol, dimethylformamide) with an aqueous solution of the immunoglobulin having thiol groups at pH 7.5.

Cytorhodin S derivatives with a thiol group introduced in which X is —NH—$R^1$—SH is capable of undergoing addition reaction with any protein or compound with maleimide group introduced. The double bond of the maleimide group is reacted with the thiol group by electrophilic addition reaction. As described below, therefore, a complex can be formed by addition of thiol group to the maleimide group in the immunoglobulin with maleimide group introduced.

The immunoglobulin to be used for preparing the complex is as described above.

Prior to the reaction of immunoglobulin with cytorhodin S with a thiol group introduced, maleimide groups are introduced into the immunoglobulin. In order to introduce the maleimide groups immunoglobulin is reacted with a maleimide compound having the formula (III)

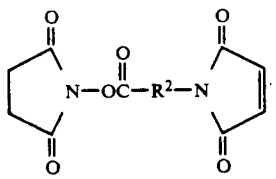

(III)

wherein $R^2$ has the same meaning as defined above to produce a maleimidated immunoglobulin having the above-mentioned formula (V). Preferred examples of the maleimide compound (III) are N-γ-maleimidobutyryloxysuccinimide and others as set forth above.

The maleimide compound (III) forms an amide bond with amino groups in the immunoglobulin by nucleophilic substitution reaction to produce a maleimidated immunoglobulin of the formula (V)

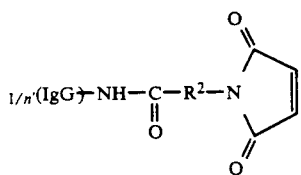

and, as a by-product, N-hydroxysuccinimide.

Depending upon the amount of the maleimide compound (III), the maleimide group is introduced in a proportion of 1-20 and preferably 5-20 per molecule of the immunoglobulin. The introduction, however, does not result in loss of the activity of immunoglobulin as antibody.

The immunoglobulin complexes of the invention are prepared by reacting the immunoglobulin (V) with maleimide groups introduced with the cytorhodin S with a thiol group introduced.

The reaction is easily carried out by mixing at pH 7.5 a solution of the thiol group-introduced cytorhodin S in a water-miscible solvent (for example, methanol, ethanol, dimethylformamide or the like) or a buffer solution at pH 7.5 (the same one as used for dissolving immunoglobulin) with an aqueous solution of the maleimide group-introduced immunoglobulin.

The cytorhodin S derivatives in which X is —NH—R¹—COOH are capable of binding with amino groups of a protein or compound by peptide bonding by means of an appropriate condensing agent. The peptide bond is formed by nucleophilic reaction of an active ester of the carboxyl group formed by the condensing agent with the amino group in the protein or the compound.

Therefore, a complex can be formed by introducing cytorhodin S derivative via peptide bond with the newly introduced carboxyl group into the amino group (side chain such as lysine residue) contained originally in immunoglobulin.

The cytorhodin S derivatives in which X is —NH—R¹—COOH are converted to an active ester by a condensing agent to form a complex. In order to prepare the active ester the cytorhodin S derivative in which X in the above-mentioned formula (I) is —NH—R¹—COOH is reacted with a carbodiimide.

As preferred examples of the carbodiimide are mentioned dicyclohexylcarbodiimide, 1,3-dimethylaminopropyl)-3-ethylcarbodiimide hydrochloride, diethylcarbodiimide, diphenylcarbodiimide, dibenzylcarbodiimide, cianamide and the like. The reaction is carried out by reacting a solution of the cytorhodin S derivative with the carbodiimide in a water-miscible organic solvent (for example, methanol, ethanol, dimethylformamide or the like) or in a buffer solution at pH 7.5 (the same one as used for dissolving immunoglobulin) at room temperature for one hour followed by addition of the reaction mixture to an aqueous solution of the immunoglobulin at pH 7.5.

Depending upon the amount of the cytorhodin S derivative to be used for the reaction the cytorhodin S derivative is bonded in a proportion of 1-20 and preferably 5-20 per molecule of the immunoglobulin. The bonding, however, does not result in loss of the activity of globulin as antibody.

The binding ratio of cytorhodin S to immunoglobulin in the complex of the invention is 1-15 : 1, that is, 1-15 molecules of cytorhodin S are bound per molecule of immunoglobulin.

Such a high proportion of the anticancer component is effective in producing high anticancer activities.

The clinical dose for the cytorhodin S derivative of the invention may be varied depending upon the route of administration and is in the range from 1 to 20 mg per day in adults in terms of the cytorhodin S.

It may be applied by intravenous, intraperitoneal or rectal route of administration. In the case of intravenous administration, an intravenous drip is also applicable in addition to the usual intravenous injection.

Pharmaceutical preparations containing the cytorhodin S derivative (I) are prepared by a conventional method using conventional carriers and additives.

The injectable preparation may for example, be a powdery preparation for injection. It is prepared by adding one or more appropriate excipients such as for example, mannitol, sucrose, lactose, maltose, glucose and fructose to the cytorhodin S derivative (I), dissolving the mixture in water, and dividing the solution into vials or ampules followed by lyophilization and sealing.

The rectal preparation may be prepared from a lipophilic base such as the semisynthetic base prepared by mixing cacao oil or a fatty acid triglyceride with a fatty acid monoglyceride or a fatty acid diglyceride in various proportions or a hydrophilic base such as a polyethylene glycol or glycerogelatin, by warming the mixture to a solution and adding the solution to a homogenous blend and forming the preparation in a mold.

Examples of the invention will be given below.

EXAMPLE 1

In 2 ml of methanol was dissolved 10 mg of cytorhodin S. To the solution were added a methanol solution (concentration 10 mg/ml) of 5.8 mg of ammonium acetate which corresponds to 10 molar equivalents of the cytorhodin S and a methanol solution (concentration 10 mg/ml) of 1.4 mg of sodium cyanoborohydride which corresponds to 3 molar equivalents. The mixture was reacted at 25° C. for 4 hours. The reaction mixture was poured into 20 ml of cooled 0 5% aqueous acetic acid, and the mixture was extracted with two portions of 5 ml of dichloromethane to remove unreacted cytorhodin S. The resulting aqueous acetic-acid solution was adjusted to pH 8 with saturated aqueous solution of sodium bicarbonate. The aqueous solution was extracted with three portions of 20 ml of dichloromethane to give an amino derivative. The dichloromethane solution was dried over anhydrous sodium sulfate, and the dichloromethane was removed under vacuum distillation. There was obtained 4.8 mg of an amino derivative of cytorhodin S (called aminocytorhodin S hereinbelow). The product was analyzed by high-pressure liquid chromatography for purity. The conditions are as follows: Column, SSC-Aquasil PE-2, 4.6 mm×250 mm (Senshu Kagaku); solvent, 2.0% triethylammonium phosphate (pH 3), 75% and acetonitrile, 25%; retention time, cytorhodin S (25.0 min.), aminocytorhodin S (12.9 min.). In addition the mass number was measured for said cytorhodin S derivative obtained by HPLC by means of an FAB/MS spectrometer (Nihon Denshi JMS-DX300) to produce a mass spectrum of 942 ($M+H^+$), which was identical with the mass number as calculated.

In the absorption spectrum of the derivative was observed a specific absorption at 495 nm derived from the anthracyclin ring of cytorhodin S. This exhibits the same spectrum as that of the starting cytorhodin S thereby indicating that anticancer activities are not lost in the derivative.

EXAMPLE 2

In 2 ml of dichloromethane was dissolved 4.8 mg of the aminocytorhodin S produced in Example 1. To the solution was added a dichloromethane solution (concentration 10 mg/ml) of 3.8 mg of γ-maleimidobutyryloxysuccinimide (manufactured by Behring Diagnostics, called GMBS hereinbelow) which corresponds to 5 molar equivalents of the aminocytorhodin S. The mixture was reacted at 25° C. for 2 hours. The reaction mixture was purified by preparative thin layer chromatography to afford a GMBS derivative of cytorhodin S. Conditions for the thin layer chromatography are as follows: thin layer plate, 2 mm silica gel 60F-254 (manufactured by Merck); developing solvent, methanol : dichloromethane =1 : 4; Rf value, the GMBS derivative (0.82), the aminocytorhodin S (0.29). The GMBS derivative thus produced was extracted from the thin layer plate, the extract was dried over anhydrous sodium sulfate, and the solvent was removed by vacuum distillation. There was obtained 2.7 mg of the GMBS derivative of cytorhodin S.

Furthermore, purity of the GMBS derivative was analyzed by HPLC, and purification was done. The column and conditions employed for the analysis are as follows column, SSC-Aquasil PE-2, 4.6 mm×250 mm (Senshu Kagaku); solvent, acetonitrile was added in 2.0% triethylammonium phosphate (TEAP, pH 3.0) over a period of 30 min. in a 0%–30% linear gradient fashion and the state of 30% acetonitrile was continued for additional 30 min.; flow rate, 1 ml/min.; retention time, 36 min. for cytorhodin S and 38 min. and 38.6 min. for the GMBS derivative. The column and conditions employed for the purification are as follows: Column, Senshu Pak NP-318-4252, 10 mm×250 mm (Senshu Kagaku); solvent, acetonitrile in 2.0% TEAP (pH 3.0) was added over a period of 20 min. in a 10%–30% linear gradient fashion and the state of 30% acetonitrile was continued for additional 15 min. In the same way, a change was made over a period of 5 min. in a 30%–100% gradient; flow rate, 4 ml/min.; retention time, 28 min. and 28.5 min. for the GMBS derivative. Eluate from the HPLC was subjected to SEP-PAK ($C_{18}$) cartridge (manufactured by Nihon Waters) to adsorb the cytorhodin S derivative, followed by washing with 0.5% aqueous acetic acid and elution with 0.5% acetic acid-methanol solution. The eluate was recovered and dried under reduced pressure to give ca. 3.2 mg of the GMBS derivative. Purity of the product was again assayed by HPLC under the same conditions as described above.

Furthermore, mass number of said cytorhodin S derivative obtained by the HPLC was measured by means of an FAB/MS spectrometer (manufactured by Nihon Denshi, JMS-DX300) to give a mass spectrum of 1215 ($M+H^+$), which was confirmed to be the mass number as calculated and was the mass number of a complex with thioglycerol employed in the measurement of mass spectrum. Also, absorption spectrum of the derivative well maintained the specific absorption of the anthracyclin ring around 495 nm.

Besides, introduction of the maleimide group was again confirmed by the reaction with aminoethanethiol which changed the spots and peak positions on TLC and HPLC. The column and conditions of the HPLC employed for the analysis are the same as described above. Retention time: 19.5 min. and 20.5 min. for the aminocytorhodin S and 23 min. and 23.5 min. for the GMBS derivative aminoethanethiol adduct. (As a control experiment, a mixture of the starting aminocytorhodin S with aminoethanethiol made under the same conditions as with the GMBS derivative was reacted. It was found that the aminocytorhodin S was not affected at all for its peak of the HPLC by the incorporation of the thiol.)

EXAMPLE 3

In 1 ml of 50 mM phosphate buffer solution (pH 7.5) containing 1 mM EDTA was dissolved 18 mg of rabbit immunoglobulin (manufactured by Sigma). To the solution was added 10 μl of 100 mM dimethylformamide solution of N-succimidyl-S-acetyl thioacetate (manufactured by Behring Diagnostics, called SATA hereinbelow), and the mixture was reacted at 25° C. for 20 min. To the reaction mixture was added 50 μl of 1M tris hydrochloride solution (pH 7.8), and the mixture was allowed to stand at 25° C. for 5 min. The reaction mixture was then fractionated on a PD-10 column (manufactured by Pharmacia) pre-equilibrated with 50 mM phosphate buffer solution (pH 7.5) containing EDTA. There was obtained a SATA derivative of the immunoglobulin. To the SATA derivative was added 0.5 mM aqueous hydroxylamine solution (pH 7.5) containing 0.25 mM EDTA which corresponds to 50 equivalents of SATA. The mixture was reacted at 25° C. for 1 hour to effect deacetylation. To the above aqueous solution containing immunoglobulin with SH group introduced was added a solution of the GMBS derivative 10 time equivalent to the SH group in 20 μl of dimethylformamide, and the mixture was reacted at 5° C. for 12 hours. After completion of the reaction, the reaction mixture was fractionated on a 20 mm×400 mm column of Sephadex G-25 (manufactured by Pharmacia) equilibrated with 50 mM phosphate buffer solution (pH 7.5) containing 1 mM EDTA. There was isolated a fraction corresponding to globular protein 160,000. The eluate was monitored at 280 nm and 495 nm in order to identify protein and cytorhodin S fractions.

The cytorhodin S-immunoglobulin complex thus obtained was desalted by dialysis and lyophilized to yield 20 mg of a product. Amount of bound cytorhodin S per molecule of the immunoglobulin was calculated by absorption at 495 nm specific for cytorhodin S and dry weight of the complex to find that 5 molecules of cytorhodin S was bound per molecule of the immunoglobulin. Furthermore, 12 molecules of cytorhodin S could be bound by increasing the amount of SATA.

Figure 3:
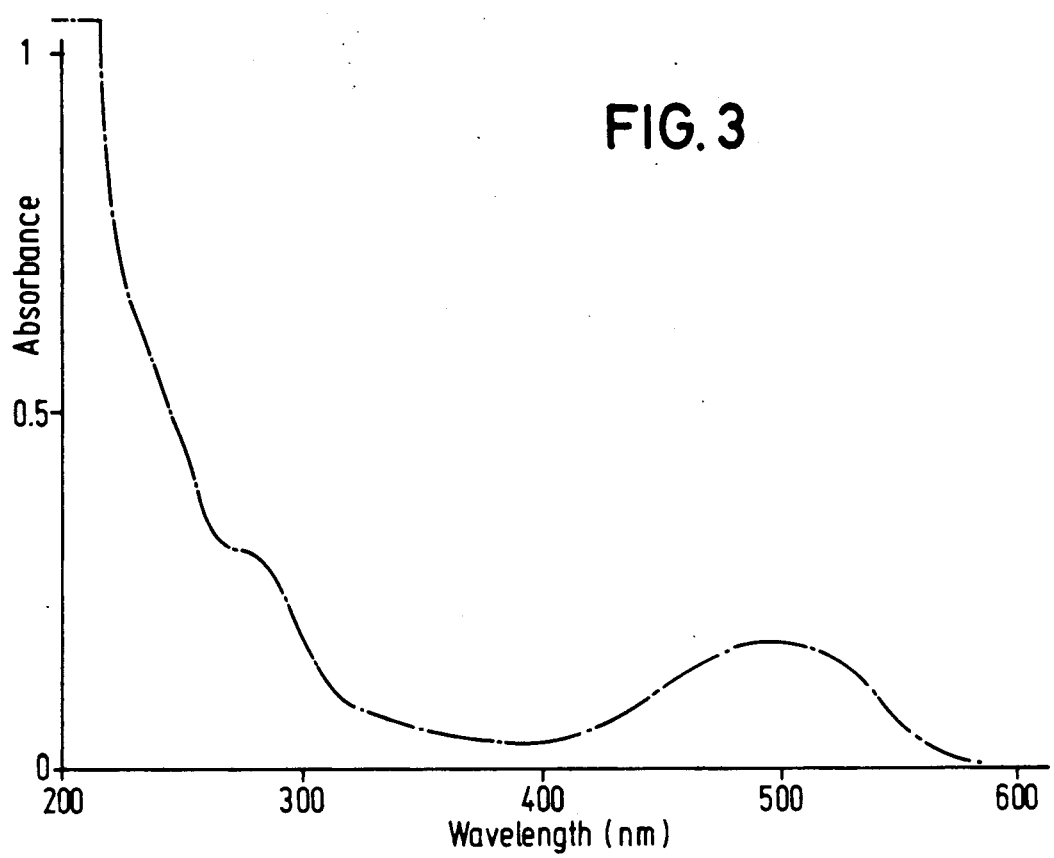
FIG. 3 shows UV spectrum of the cytorhodin S-immunoglobulin complex.

FIG. 3 shows UV spectrum of the complex in which approximately 12 molecules of cytorhodin S are bound per molecule of the immunoglobulin. UV spectra of the complexes demonstrate that as the proportion of bound cytorhodin S is increased, the absorption maximum for cytorhodin S is increased.

EXAMPLE 4

To a solution of 5 mg of cytorhodin S in 1 ml of methanol was added a methanol solution of 2.6 mg of γ-aminobutyric acid (concentration 1 mg/ml) which corresponded to 6 moles per mole of the cytorhodin S. After adjusting the pH with triethylamine to 8, 1.4 mg of sodium cyanoborohydride which corresponded to 3 molar equivalents was added, and the mixture was reacted at 25° C. for 24 hours. The reaction mixture thus produced was confirmed by TLC for the presence or absence of the product followed by analysis of the purity by HPLC and purification. Rf values on the TLC under the same conditions as in Example 2 were 0.57 for cytorhodin S and 0.28 for the γ-aminobutyrate derivative. Retention times in the HPLC analysis under the same conditions as in Example 2 were 36 min. for cytorhodin S and 29 min. for the γ-aminobutyrate derivative. Purification by HPLC under the same conditions as Example 2 yielded ca. 1.5 mg of the γ-aminobutyrate derivative.

Furthermore, measurement of the mass number of said derivative by means of an FAB/MS spectrometer (JMS-DX300) gave a mass spectrum of 1028 (M+H+) which was identical with the mass number as calculated.

Besides, absorption spectrum of the derivative well retained the specific absorption around 495 nm for the anthracyclin ring of cytorhodin S.

EXAMPLE 5

To a solution of 2.5 mg of cytorhodin S γ-aminobutyrate derivative in DMF (concentration 50 mg/ml) was added a DMF solution of 515 μg of dicyclohexylcarbodiimide (concentration 50 mg/ml) which corresponded to an equimolar amount to the cytorhodin S derivative. The mixture was reacted at room temperature for 1 hr.

To a solution of 20 mg of rabbit immunoglobulin (manufactured by Sigma) in 1 ml of 50 mM phosphate buffer solution (pH 7.5) was added the above-prepared DMF solution of the cytorhodin S derivative. The mixture was reacted at room temperature for 30 min. The cytorhodin S γ-amino-butyrate derivative corresponds to 20 molar equivalents to the rabbit immunoglobulin. Then, 1M tris-hydrochloric acid buffer solution (pH 7.8) was rapidly added, and the mixture was stirred and allowed to stand for 10 min. The resulting mass was subjected to a PD-10 column (manufactured by Pharmacia) pre-equilibriated with 50 mM phosphate buffer solution for separation and purification.

EXAMPLE 6

To a solution of 5 mg of cytorhodin S in 1 ml of methanol were added 1 molar aqueous acetic acid solution of 3.3 mg of lysine (concentration 10 mg/ml) which corresponded to 6 molar equivalents to the cytorhodin S and 1 4 mg of sodium cyanoborohydride which corresponded to 3 molar equivalents. The mixture was reacted at 25° C. for 24 hrs. The reaction mixture thus obtained, after confirmed for the presence or absence of the product, was analyzed by HPLC for purity followed by purification. Rf value for the lysine derivative on the TLC under the same conditions as in Example 2 was 0.20. Retention time for the lysine derivative in the HPLC analysis under the same conditions as in Example 2 was 27 min. and 28 min. Purification by HPLC under the same conditions as in Example 2 yielded ca. 2.6 mg of the lysine derivative.

Furthermore, mass number of said derivative was measured by means of a FAB/MS spectrometer (JMS-DX300) to give a mass spectrum of 1071 (M+H+) which was identical with the mass number as calculated.

Besides, absorption spectrum of the derivative well retained a specific absorption around 495 nm for the anthracyclin ring of cytorhodin S.

EXAMPLE 7

To a solution of 5 mg of cytorhodin S in 1 ml of methanol were added a methanol solution of 1.7 mg of aminoethanethiol (concentration 1 mg/ml) which corresponded to 6 molar equivalents to the cytorhodin S and 1.4 mg of sodium cyanoborohydride which corresponded to 3 molar equivalents. The mixture was reacted at 25° C. for 24 hrs. The reaction mixture thus obtained, after confirmed by TLC for the presence or absence of the product, was analyzed by HPLC for purity followed by purification. Rf value for the aminoethanethiol derivative on the TLC under the same conditions as in Example 2 was 0.25. Retention time for the aminoethanethiol derivative in the HPLC analysis under the same conditions as in Example 2 was 28 min. Purification by HPLC under the same conditions as in Example 2 yielded ca. 1.6 mg of the aminoethanethiol derivative.

Furthermore, mass number of said derivative was measured by means of a FAB/MS spectrometer (JMS-DX300) to give a mass spectrum of 1002(M+H+) which was identical with the mass number as calculated.

Besides, absorption spectrum of the derivative well retained a specific absorption around 495 nm for the anthracyclin ring of cytorhodin S.

On the other hand, the introduction of the —SH group was again confirmed by the reaction with N-ethylmameimide thereby changing the spots and peak positions of TLC and HPLC. (The changes observed with the aminoethanethiol derivative were not observed with cytorhodin S and aminocytorhodin S.)

EXAMPLE 8

To a solution of 5 mg of cytorhodin S in 1 ml of methanol were added a methanol solution of 2.7 mg of cysteine (concentration 1 mg/ml) which corresponded to 6 molar equivalents to the cytorhodin S and 1.4 mg of sodium cyanoborohydride which corresponded to 3 molar equivalents. The mixture was reacted at 25° C. for 24 hrs. The reaction mixture thus obtained, after confirmed by TLC for the presence or absence of the product, was analyzed by HPLC for purity followed by purification. Rf value for the cysteine derivative by the TLC under the same conditions as in Example 2 was 0.35. Retention time for the cysteine derivative in the HPLC analysis under the same conditions as in Example 2 was 32 min. Purification by HPLC under the same conditions as in Example 2 yielded ca. 1.8 mg of the cysteine derivative.

Furthermore, mass number of said derivative was measured by means of a FAB/MS spectrometer (manufactured by Nihon Denshi) gave a mass spectrum of 1046 (M+H+) which was identical with the mass number as calculated.

Besides, the introduction of —SH group was confirmed in the same way as in Example 7 by the reaction with N-ethylmaleimide thereby changing the spots and peak positions (TLC and HPLC).

EXAMPLE 9

To a solution of 11 mg of rabbit immunoglobulin (manufactured by Sigma) in 1 ml of 50 mM phosphate buffer solution (pH 7.5) containing lmM ETDA was added a DMF solution of 191 μg of N-γ-maleimidobutyryloxysuccinimide (manufactured by Behring Diagnostics, called GMBS hereinbelow)(concentration 50 mg/ml). The mixture was reacted at 25° C. for 2 hrs. To the reaction solution was added 50 μl of 1M tris-hydrochloric acid buffer solution (pH 7.8), and the mixture was allowed to stand at 25° C. for 5 min. The reaction mixture was then fractionated by a PD-10 column (manufactred by Pharmacia) pre-equibriated with 50 mM phosphate buffer solution (pH 7.5) containing 1 mM EDTA to give a rabbit immunoglobulin of maleimide-introduced type.

The cytorhodin S derivative of —SH group-introduced type previously produced in Example 7 was reacted with the rabbit immunoglobulin of maleimide-introduced type.

A solution of 1.5 mg of the cytorhodin S aminoethanediol derivative in DMF (concentration 100 mg) which corresponded to 2 molar equivalents to the maleimide group introduced into rabbit immunoglobulin was added to an aqueous solution of the rabbit immunoglobulin of maleimide-introduced type prepared above. The mixture was reacted at 5° C. for 12 hrs.

EXAMPLE 10

To a solution of 5 mg of cytorhodin S in 1 ml of methanol were added a methanol solution of 3.2 mg of gylcine ethyl ester (concentration 1 mg/ml) which corresponded to 6 molar equivalents to the cytorhodin S and 1.4 mg of sodium cyanoborohydride which corresponded to 3 molar equivalents. The mixture was reacted at 25° C. for 24 hrs. The reaction mixture thus obtained, after confirmed by TLC for the presence or absence of the product, was analyzed by HPLC for purity followed by purification. Rf value for the glycine ethyl ester derivative on the TLC under the same conditions as in Example 2 was 0.34. Retention time for the glycine ethyl ester derivative in the HPLC analysis under the same conditions as in Example 2 was 32 min. and 33 min. Purification by HPLC under the same conditions as in Example 2 yielded ca. 1.4 mg of the glycine ethyl ester derivative.

Furthermore, mass number of said derivative was measured by means of a FAB/MS spectrometer (JMS-DX300) to give a mass spectrum of 1028 (M+H+) which was indentical with the mass number as calculated.

Also, absorption spectrum of the derivative well retained a specific absorption around 495 nm for the anthracyclin ring of cytorhodin S.

EXAMPLE 11

Female BALB/C mice 7-10 weeks old were administered intraperitoneally with 25 μg of purified human CEA per mouse together with complete Freund's adjuvant. After 10 weeks, a solution of 25 μg of CEA in physiological saline solution was intravenously administered. On the 3rd day after the administration the spleen was isolated, and the spleen cells were fused with nonproductive type myeloma cell X63-Ag 8,653. The cell fusion and subsequent cultivation and cloning were carried out basically according to the method of Oi et al. (Oi V. T. & Herzenberg, L.A., Selected methods in Cellular Immunology, B.B. Mishell & S. M. Shiigi Eds, p. 351, Freeman & Co., San Francisco 1980). The ratio of the spleen cell to the myeloma cell was 10:1. The mixture was centrifuged for a short period of time to give a pellet. To the pellet was dropwise added 0.5 ml of 42.5% polyethylene glycol (MW 2,000, containing 15% dimethylsulfoxide), and the mixture was slowly stirred at 37° C. for 2 min. The resulting mixture was dilluted 20:1 with RPMI medium. After centrifuged, it was suspended in RPMI-1640 medium containing bovine embryonic serum. The suspension was distributed in a 96-well microtiter plate in an amount of $5 \times 10^5$ cells each. After cultivated at 37° C. overnight, one drop of HAT medium (100 μM hypoxanthine, $4 \times 10^{-4}$ μM aminopterine, $1.6 \times 10^{-2}$ thymidine) each was added. The selection of hybridoma by means of HAT medium was conducted on the 2nd, 3rd, 5th, 7th, 10th and 13th day by exchanging half of the medium in each well with fresh HAT medium. Anti-CEA activity of the supernatant from the culture was assayed by RIA or EIA. The cells assayed active were transferred to a larger culture system or cloned by means of a limiting dilution method. The fused cells thus obtained were transplanted into the peritoneal of mice of the same strain in advance treated with 0.5 ml of tetramethylpentadecane. One to two weeks after the transplantation, a few ml of ascites was obtained in which homogeneous monoclonal antibody was contained at a concentration of 5-10 mg/ml.

A cytorhodin S complex with the monoclonal antibody against CEA (MA 204) thus obtained was prepared in the same way as in Example 3.

Test for anticancer activity of the cytorhodin S-immunoglobulin complex

Figure 4:
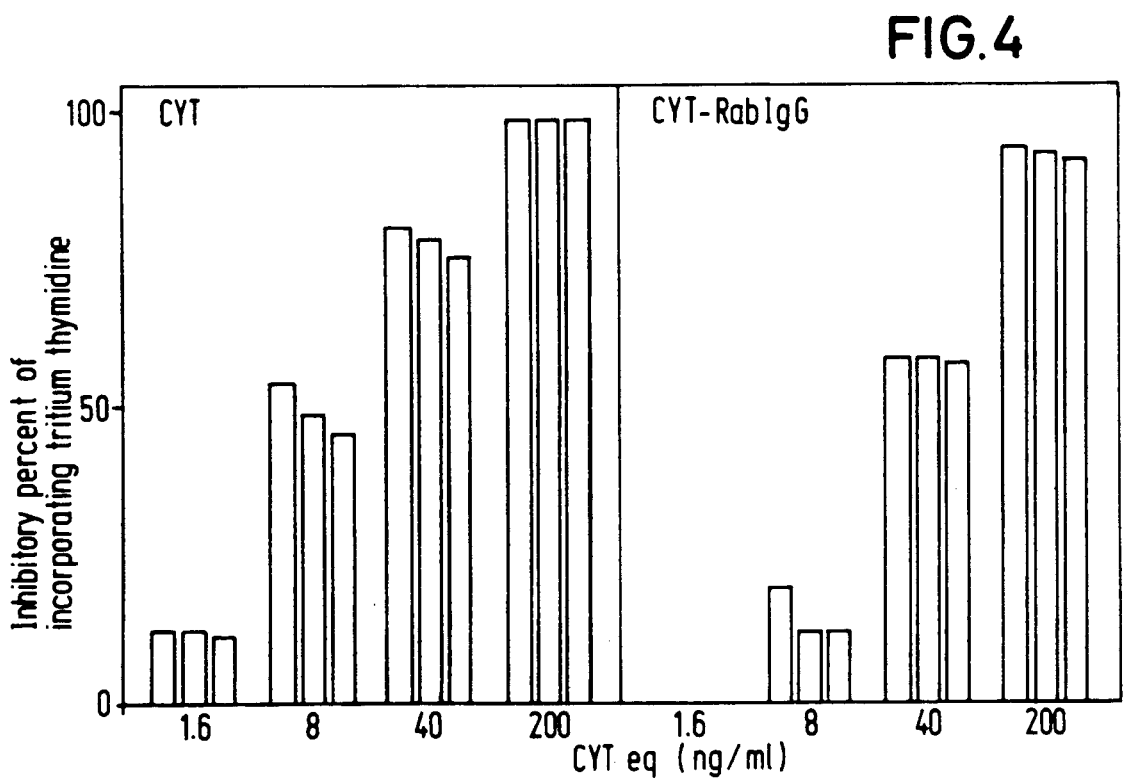
FIG. 4 graphically shows cell growth-inhibiting activities of cytorhodin S and the cytorhodin S-rabbit immunoglobulin complex against L1210 cells.

In a 96-well micro plate was distributed 200 μl of tumor cell line L1210 ($5 \times 10^4$ cells/ml) cultivated in RPMI 1640-10% fetal calf serum ($1 \times 10^4$ cells/well). To the cell culture were added 10 μl each of cytorhodin S (CYT) and cytorhodin S-immunoglobulin complex (CYT-rabbit IgG). The mixture was incubated at 37° C. for 18 hours. Then, 25 μl of tritium-labeled thymidine was added at a concentration of 0.5 μCi/well, and the mixture was incubated at 37° C. for 6 hours. Subsequently, the cells were collected on a filter by a cell collector, dried and amount of the labeled thymidine incorporated into the cell was determined by means of a liquid scintillation counter for comparison of DNA-synthesizing activity of the cell. The results are shown in FIG. 4. FIG. 4 demonstrates that the anticancer acitivity of CYT is approximately maintained in CYT-rabbit IgG.

Figure 5:
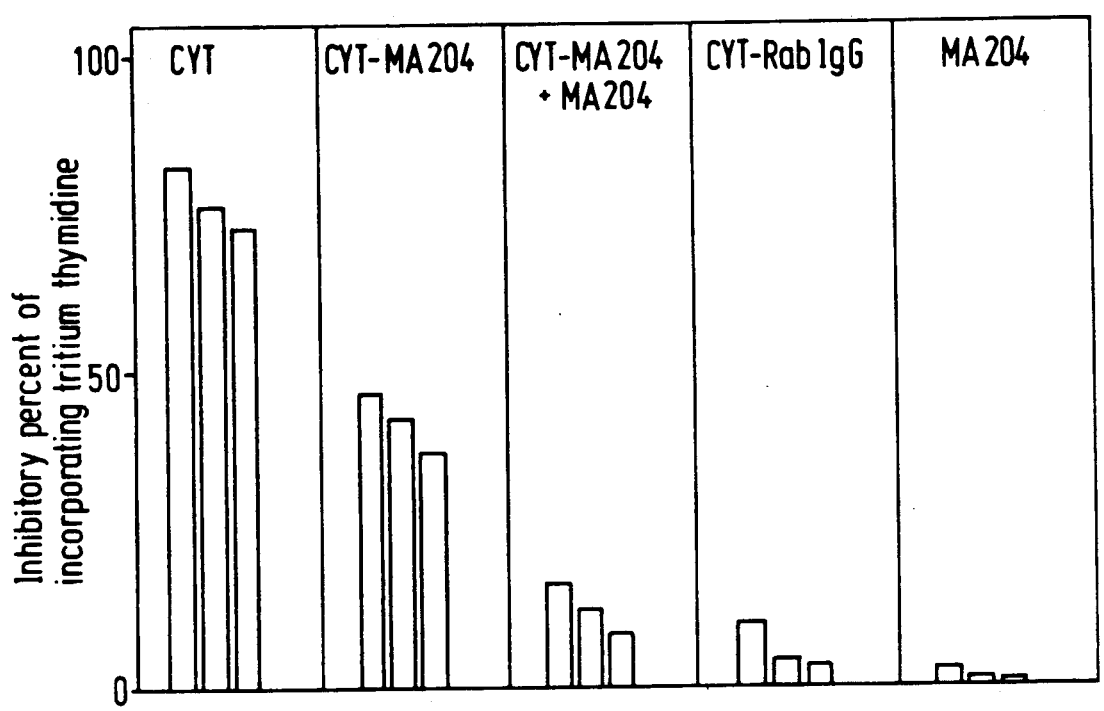
FIG. 5 graphically shows cell growth-inhibiting activities of cytorhodin S, the cytorhodin S-MA 204 immuno complex, the cytorhodin S-rabbit immunoglobulin complex and control against Colo 205 cells.

Similarly, effect of the cytorhodin S derivative (cytorhodin S-anti CEA monoclone antibody complex) was tested for Colo 205 which is a CEA-producing cell. The results are shown in FIG. 5. Amounts of the test materials used are as follows:

| Samples | Drugs/Antibodies | Ratio |
|---------|------------------|-------|
| CYT | 0.2 μg/ml | |
| CYT-MA 204* | 0.2 μg**/6.3 μg/ml | 2:1 |
| CYT-Rab IgG | 0.2 μg*/12.5 μg/ml | 2:1 |
| MA 204* | 0.5 μg/ml | |
| Cell | Colo 205, 5 × 10⁴/well | |

*MA 204 is anti CEA monoclone antibody.
**indicates CYT-activity equivalent (CYT eq.)

Since MA 204 is higher in selection specificity than Rab IgG, the higher cell growth-inhibiting activity of CYT-MA 204 than that of CYT-Rab IgG shown in FIG. 5 suggests that the cytorhodin S-immunoglobulin complex of the invention selectively acts on cancer cells.

Comparison with aclacinomycin-immunoglobulin complex

For comparison, an immunoglobulin complex with aclacinomycin A

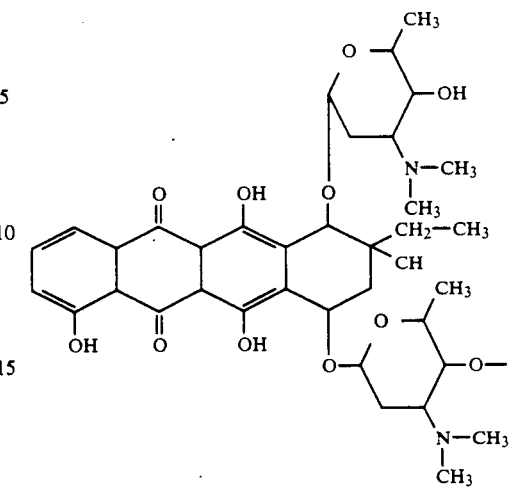

Figure 6:
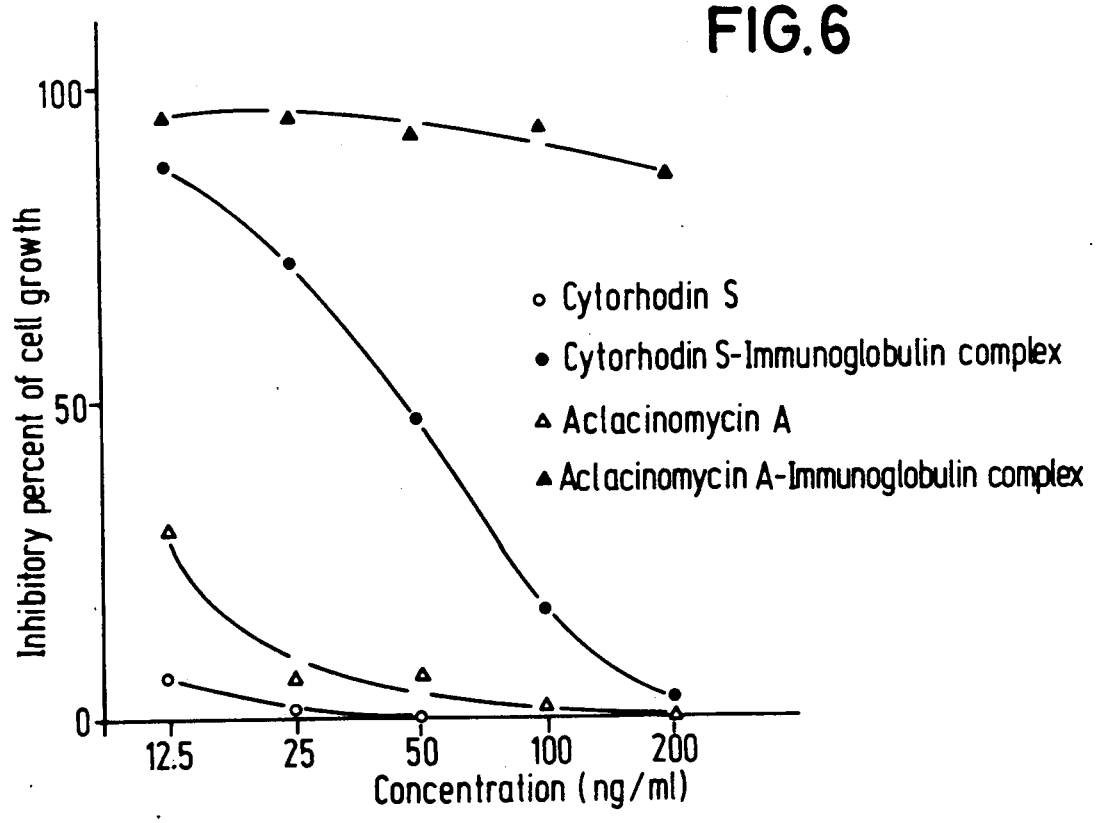
FIG. 6 graphically shows cell growth-inhibiting activities of the cytorhodin S-immunoglobulin complex and the aclacinomycin immunoglobulin complex against L1210 cells.

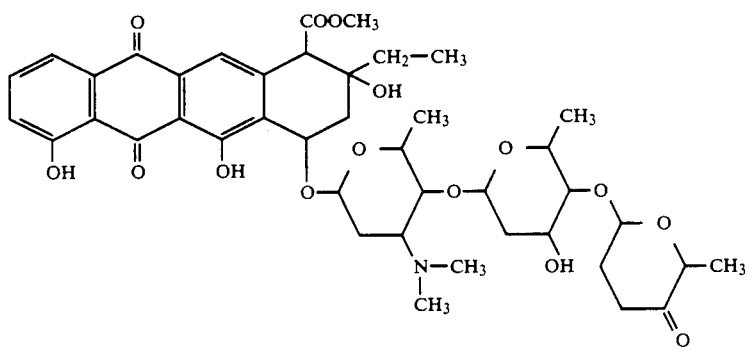

which is structurally similar to cytorhodin S was prepared in the same way as in Example 3. Whereas cytorhodin S was added in a proportion of 5-12 molecules per molecule of the antibody, aclacinomycin was added in a proportion as small as 2 molecules per molecule of the antibody. DNA synthesis-inhibiting activity of the two antibody complexes in L1210 was determined in terms of the amount of tritium-labeled thymidine incorporated into the cells. The results are shown in FIG. 6. FIG. 6 demonstrates that the activity of the cytorhodin S complex against the cells was higher than that of the aclacinomycin complex.

What is claimed is:
1. A compound represented by the formula I

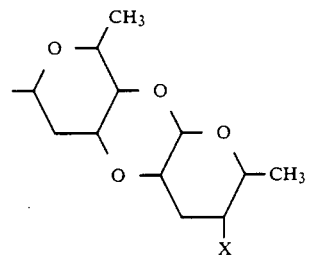

wherein X is selected from the group consisting of the formulae
a) —NH₂ or —NH—(CH₂)₂—SH,
b)

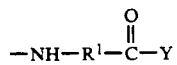

wherein R¹ is unsubstituted C₁-C₅-alkylene which is substituted with NH₂ or SH, and Y is OH, C₂H₅—or the radical NH—(—IgG)₁/ₙ, wherein IgG represents an immunoglobulin moiety and n represents an integer of 1-15, (c)

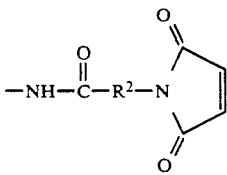

wherein $R^2$ is lower alkylene, phenylene, $C_4$-$C_7$-cycloalkylene phenylenyl lower alkyl or $C_4$-$C_7$-cycloalkylenyl lower alkyl, d)

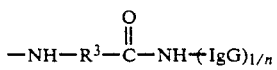

wherein $R^3$ is a radical of the formula

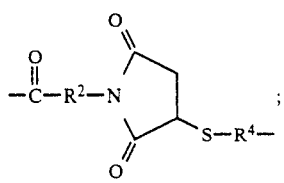

wherein $R^2$ is a hereinabove described, and $R^4$ is lower alkylene, phenylene, $C_4$-$C_7$-cycloalkylene, phenylenyl lower alkyl or $C_4$-$C_7$-cycloalkylenyl lower alkyl, wherein IgG represents an immunoglobulin moiety and n represents an integer of 1-15, and e)

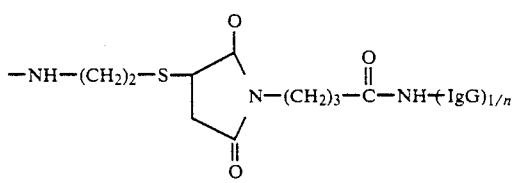

wherein IgG represents an immunoglobulin moiety and n represents an integer of 1-15 and a salt thereof.

2. A cytorhodin S derivative as claimed in claim 1, wherein said lower alkylene group is methylene, ethylene or propylene; said phenylene group is p-phenylene or m-phenylene; said $C_4$-$C_7$ cycloalkylene group is cyclohexylene; said phenylenyl lower alkyl group is a phenylenyl-methyl; and said $C_4$-$C_7$ cycloalkenyl lower alkyl group is cyclohexylenyl-methyl.

3. A cytorhodin S derivative according to claim 1, wherein $R^1$ is a methylene group.

4. A cytorhodin S derivative according to claim 1, wherein said $R^1$ is a ethylene group.

5. A cytorhodin S derivative according to claim 1, wherein said $R^1$ is a propylene group.

6. A cytorhodin S derivative according to claim 1, wherein said $R^1$ is a ethylene group that is substituted with a $-NH_2$ group.

7. A cytorhodin S derivative according to claim 1, wherein said $R^1$ is a pentene that is substituted with a $-NH_2$ group.

8. A compound as defined in claim 1, wherein $R^2$ is a propylene group and $R^4$ is a methylene group.

9. A compound as defined in claim 1, wherein n is an integer of 5-12.

10. A compound as defined in claim 1 wherein immunoglobulise moiety the IgG is a moiety of the antibody against carcinoembryonic antigen (CEA).

11. A process for preparing a cytorhodin S derivative of formula (I) as defined in claim 1, wherein X is $-NH_2$, $-NH-(CH_2)_2-SH$ or $-NH-R^1-CO-Y$, wherein $R^1$ is unsubstituted $C_1$-$C_5$-alkylene or $C_1$-$C_5$-alkylene which is substituted with $NH_2$ or SH, and Y is OH, $C_2H_5$- or the radical $NH-(-IgG)_{1/n}$ wherein IgG represents an immunoglobulin moiety and n represents an integer of 1-15, which comprises the step of reducing a cytorhodin S having the formula (II)

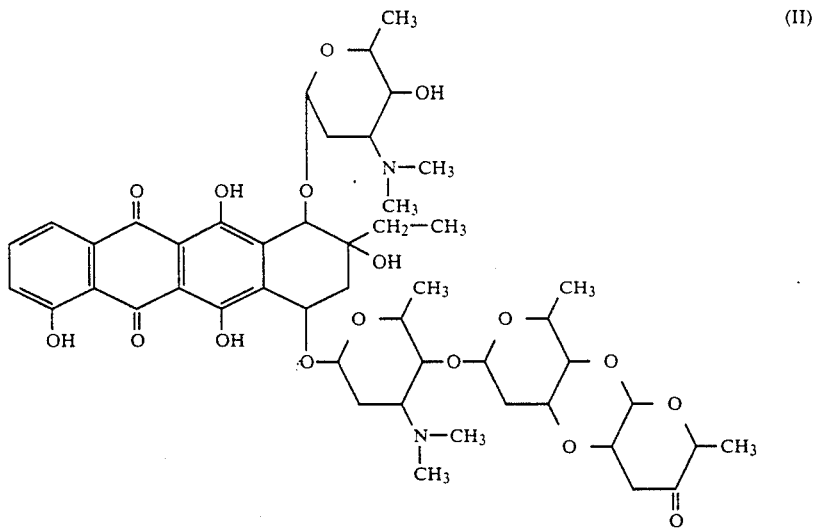

with an alkali metal cyanoborohydride in the presence of an ammonium salt or a compound of the formula $NH_2-(CH_2)_2-SH$ or a compound of the formula

where $R^1$ and Y are as hereinbefore described.

12. The process for preparing a cytorhodin S derivative of the formula (I) as defined in claim 1, wherein X is a group of the formula

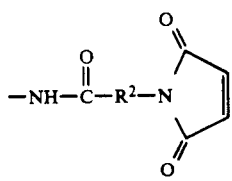

wherein $R^2$ is lower alkylene, phenylene, $C_4$-$C_7$-cycloalkylene, phenylene lower alkyl or $C_4$-$C_7$-cycloalkylenyl lower alkyl, which comprises reacting a compound of the formula (I), as defined in claim 1, wehrein X is —NH$_2$, with a maleinimide compound having the formula (III)

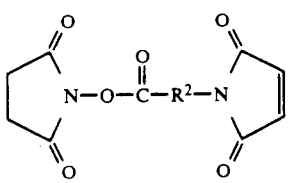

wherein $R^2$ is as hereinabove described.

13. The process for preparing a cytorhodin S derivative of the formula (I) as defined in claim 1, wherein X is a group of the formula

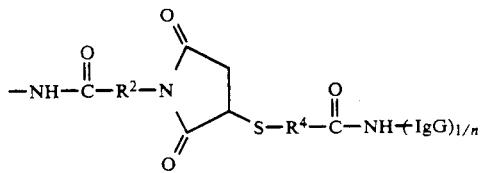

wherein $R^2$ and $R^4$ are each independently lower alkylene, phenylene, $C_4$-$C_7$-cycloalkylene, phenylene lower alkyl or $C_4$-$C_7$-cycloalkylenyl lower alkyl, IgG represents an immunoglobulin moiety and n represents an integer of 1-15, which comprises reacting a compound of the formula (I) as defined in claim 1, wherein X is a group of the formula

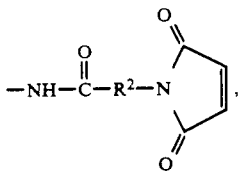

wherein $R^2$ is as hereinbefore described, with a thiolated immunoglobulin having the formula (IV)

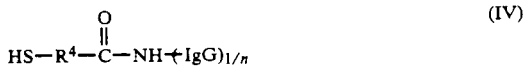

wherein $R^4$, IgG and n are as hereinbefore described.

14. The process for preparing a cytorhodin S derivative of the formula (I) as defined in claim 1, wherein X is a group of the formula

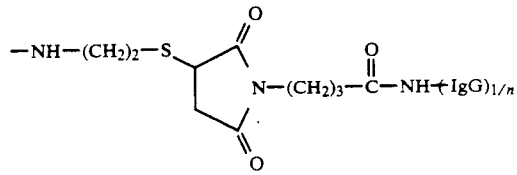

wherein IgG represent an immunoglobulin moiety and n represents an integer of 1-15, which comprises reacting a compound of the formula (I) as defined in claim 1, wherein X is the group —NH—(CH$_2$)$_2$—SH, with a maleinimidated immunoglobulin having the formula (IV)

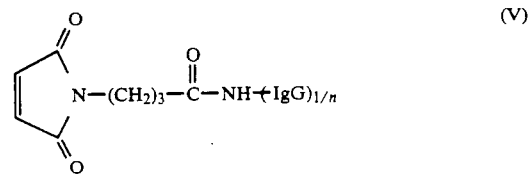

wherein IgG and n are as hereinbefore described.

15. The process for preparing a cytorhodin S derivative of the formula (I) as defined in claim 1, wherein X is

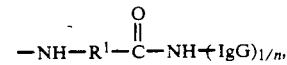

wherein $R^1$ is unsubstituted $C_1$-$C_5$-alkylene or $C_1$-$C_5$-alkylene which is substituted with NH$_2$ or SH, and wherein IgG represents an immunoglobulin moiety and n represents an integer from 1-15, which comprises reacting a compound of the formula (I) as defined in claim 1, wherein X is NH—$R^1$-COOH and $R^1$ is as hereinbefore described, with an immunoglobulin having the formula (VI)

wherein IgG and n are as hereinbefore described.

* * * * *